United States Patent [19]

Poultney et al.

[11] Patent Number: 4,724,326

[45] Date of Patent: Feb. 9, 1988

[54] OFF-CHIP TIME-DELAYED INTEGRATION AREA ARRAY FRAUNHOFER LINE DISCRIMINATOR

[75] Inventors: Sherman K. Poultney, Wilton; Hans G. Sippach, New Fairfield; Joseph H. Oberheuser, Trumbull, all of Conn.

[73] Assignee: The Perkin-Elmer Corporation, Norwalk, Conn.

[21] Appl. No.: 871,057

[22] Filed: Jun. 5, 1986

[51] Int. Cl.⁴ ............................................. G01N 21/64
[52] U.S. Cl. ................................. 250/458.1; 250/253; 250/332; 250/370; 356/318
[58] Field of Search ............. 250/459.1, 458.1, 370 G, 250/253, 332; 356/317, 318

[56] References Cited

U.S. PATENT DOCUMENTS

| | | | |
|---|---|---|---|
| 3,578,848 | 5/1971 | Austin | 350/320 |
| 3,598,994 | 8/1971 | Markle | 250/458.1 |
| 3,641,344 | 2/1972 | Markle | 250/339 |
| 3,769,516 | 10/1973 | Markle et al. | 250/363 R |
| 3,821,763 | 6/1974 | Scott | 354/94 |
| 4,054,797 | 10/1977 | Milton et al. | 250/332 |
| 4,236,071 | 11/1980 | Chimenti | 250/253 |
| 4,433,245 | 2/1984 | Poultney | 250/458.1 |
| 4,446,372 | 5/1984 | Gurnee | 250/334 |

Primary Examiner—Janice A. Howell
Assistant Examiner—Constantine Hannaher
Attorney, Agent, or Firm—Thomas P. Murphy; Edwin T. Grimes; Francis L. Masselle

[57] ABSTRACT

An apparatus for determining the fluorescence of materials in a scene which includes optical means to collect radiation from the scene. Means are provided to divide the collected radiation into first and second beam paths. The first beam path traverses a first filter centered on a Fraunhofer line and having a passband which extends into the solar continuum on either side of the Fraunhofer line. The second beam path traverses the first filter and a second filter, also centered on the Fraunhofer line, with a passband on the order of half the bandwidth, at half-depth, of the Fraunhofer line. Means are provided to image the first and second beams onto first and second detector arrays, respectively. The image on the first detector array is registered with the image on the second detector array. Co-adding means are provided whereby successive detector pixels at successive time intervals corresponding to a single point on the ground are added and averaged. The time interval is a function of a constant clock rate and a V/H signal. A single detector is provided to detect the intensity of direct solar radiation outside the Fraunhofer line. A processor compares the value of intensity from the co-added point on the ground from the first and second detector arrays and the single detector to determine fluorescence at each point on the ground in the scene being viewed. In another form, where an optical laser illuminator is employed, the first beam path traverses a first filter which only allows the laser radiation to pass. The second beam path has a passband which passes the emission spectrum of a material excited by the laser radiation.

18 Claims, 10 Drawing Figures

OFF-CHIP TIME-DELAYED INTEGRATION AREA ARRAY FRAUNHOFER LINE DISCRIMINATOR

BACKGROUND OF THE INVENTION

This invention pertains generally to a device for sensing, measuring and recording fluorescence emitted by certain materials in a scene viewed in sunlight. More particularly, the present invention relates to an apparatus which measures fluorescent radiation emitted by certain materials at unique ground points in a narrow, preselected wavelength.

The basic theory employed in Fraunhofer line discrimination is as follows. The solar spectrum contains a number of very sharp (Fraunhofer) absorption lines created in the photosphere of the sun. When sunlight is reflected, some wavelengths tend to be reflected more than others, but the variation of reflectivity with wavelength is relatively smooth across the solar spectrum. Consequently, the signature Fraunhofer lines are retained in the reflected radiation. The same is not true in the presence of fluorescence, which is characterized by a strong absorption in one spectral region followed by re-emission at longer wavelengths. Provided the bandwidth of these re-emissions encompass a Fraunhofer line wavelength they tend to remove the sharp Fraunhofer lines, again yielding a relatively smooth emission spectrum. Any addition of a fluorescence spectrum to a reflected solar spectrum therefore tends to reduce the relative depth of the Fraunhofer absorption lines near the fluorescence emission peak. Detection of this reduction of the relative depth of Fraunhofer lines yields detection of fluorescence in the scene being viewed.

Various techniques have been developed to take advantage of this phenomenon to measure fluorescence within a sunlit scene. Some of these techniques are disclosed in U.S. Pat. No. 3,769,516 which is the basis for a successful, but limited capability, Fraunhofer line discriminator (FLD). Other techniques, more similar to the present invention, are disclosed in U.S. Pat. No. 3,598,994. Both U.S. Pat. Nos. 3,769,516 and 3,598,994 have the same assignee as the present invention.

The FLD disclosed in U.S. Pat. No. 3,769,516 provides a sky telescope and an earth telescope, each of which forms radiation beams which are directed to a single optical chopper. The chopper sequentially directs each beam through a single Fabry-Perot filter centered on a Fraunhofer line and a single neutral density filter. The chopped segments are recombined to form a beam with four components: sky-looking radiation inside and outside the Fraunhofer line and earth-looking radiation inside and outside the Fraunhofer line. A single photomultiplier tube, with a blocking filter in front, receives the beam and produces corresponding sequential electrical pulses which are processed to yield fluorescence level in the scene being viewed.

While the apparatus disclosed in the U.S. Pat. No. 3,769,516 was useful in most applications it did not meet the higher performance requirements of the present generation of Fraunhofer line discriminators (FLD's). Such requirements for FLD's are enhanced sensitivity or signal-to-noise ratios, improved spatial resolution and wider coverage.

In U.S. Pat. No. 3,598,994 a bundle of sunlight is encoded and split onto two beams. Each of these beams is combined with similar beams, also, encoded, which contain solar reflected and solar excited fluorescent radiation from a scene being viewed. The two beams (each of which contain reference and sample components) are passed through two spectral filters and detected photo electrically on two separate detectors. One of the spectral filters is centered on a Fraunhofer absorption line, the other is centered a few Angstroms away in the solar continuum. The four signals, corresponding to the direct solar intensity inside and outside the Fraunhofer line and the intensity of radiation of the scene being viewed inside and outside the Fraunhofer line, are separated electronically. These four signals are then combined in an analog computer to yield a signal proportional to the fluorescence of the sample material.

While the device disclosed in the U.S. Pat. No. 3,598,994 did advance the art in this area, actual use proved difficult due to problems with the photo electric detectors. Further, the device only produces a signal indicating presence and amount of fluorescence in a scene being viewed. It does not indicate the location of fluorescent materials in a given scene nor does it indicate variations of fluorescence over different portions of the scene.

Accordingly, the present invention provides an improved Fraunhofer line discriminator which has enhanced spatial resolution, discrimination and high coverage. The manner in which the foregoing objects are achieved will be apparent from the following description and appended claims.

SUMMARY OF THE INVENTION

There is provided an apparatus for sensing fluorescent radiation emitted by a material excited by sunlight and indicating variations of fluorescence in different portions of the scene. The apparatus comprises: foreoptics, including a wide angle lens to collect light from a scene and a reflecting collimating telescope. The telescope conditions the radiation for passage through the optics of the FLD, a first channel of which is tuned to a specific Fraunhofer line, as well as a second channel where no Fraunhofer line exists. Having passed through the appropriate filters, the radiation is imaged onto first and second detector arrays corresponding to the first and second multiplexer channels. The detector arrays are registered so that corresponding elements of each array view the same region on the ground.

Successive views or frames of the scene contain many pixels in common. Co-adding of these pixels enables excellent signal-to-noise characteristics to be achieved with very modest optics. Co-adding is done off-chip, that is, not on the detector array itself, since the optical system is sized to give the maximum signal for each pixel in the detector arrays without saturating that pixel.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception on which the disclosure is based may readily be utilized as a basis for designing other structures for carrying out the several purposes of the invention. It is important, therefore, that the claims be regarded as including such equivalent structures as do not depart from the spirit and scope of the invention.

Specific embodiments of the invention have been chosen for the purposes of illustration and description and are shown in the accompanying drawing, forming a part of the specification.

DESCRIPTION OF THE PREFERRED EMBODIMENT

The preferred embodiment is described in reference to light as the incoming radiation. It can be understood by those skilled in the art that the incoming radiation can be of any wavelength, whether or not it is in the visible spectrum.

Further, while the preferred embodiment is described as being mounted on an airborne platform it can be understood by those skilled in the art that the apparatus disclosed herein can be mounted on any moving or stationary platform.

Figure 1A:
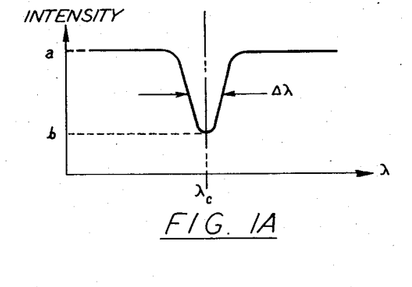
FIG. 1A is a graphical representation of light intensity versus wavelength for a sky looking collector.

FIG. 1A is a graph of light intensity versus wavelength showing light intensity of direct sunlight over a portion of the spectrum wherein lies a Fraunhofer line. The wavelength of the Fraunhofer line is designated $\lambda_c$ and its width at half-intensity is $\Delta\lambda$. Full widths at half-depth for Fraunhofer lines are typically 0.7 to 1.8 Å.

Figure 1B:
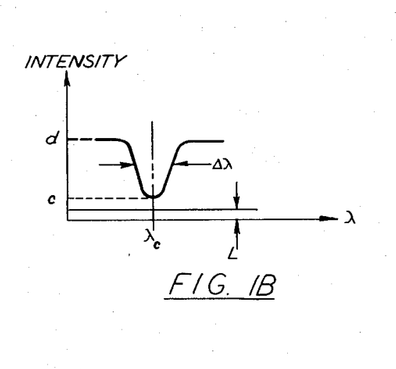
FIG. 1B is a graphical representation of light intensity versus wavelength for an earth looking collecter.

FIG. 1B is a graph of light intensity versus wavelength for an earth-looking collector. Again, $\lambda_c$ is the wavelength of the Fraunhofer line being viewed.

For FIGS. 1A and 1B:

a = light intensity for sky-looking collector outside the Fraunhofer line b = light intensity for sky-looking collector inside the Fraunhofer line c = light intensity for earth-looking collector inside the Fraunhofer line d = light intensity for earth-looking collector outside the Fraunhofer line L = Luminescence $\lambda_c$ = Wavelength of subject Fraunhofer line $\Delta\lambda$ = Width of Fraunhofer line at half-intensity.

As is known, luminescence, L, can be calculated by the following equation:

$$L = \frac{1}{a} \frac{(c - nd)}{(1 - n)} \quad (1)$$

n = a constant representative of the depth of the Fraunhofer line.

It should be noted that there are a number of materials that fluoresce in sunlight. These generally have a bandpass of several hundred angstroms. Many of these materials have associated Fraunhofer lines, i.e., the Fraunhofer lines have angstrom numbers somewhere within the wavelength range of the material to be detected. For example, aqueous solutions of Rohodamine WT dye have a bandpass of fluorescence of several hundred angstroms which encompass the Fraunhofer absorption line of 5890 Angstroms. This makes possible the detection of the fluorescence and intensity of fluorescence of the dye. An apparatus in accordance with the present invention is capable of measuring the fluorescence of the above material as well as any material which fluoresces in sunlight for which there is a Fraunhofer line located in its wavelength range.

Figure 2:
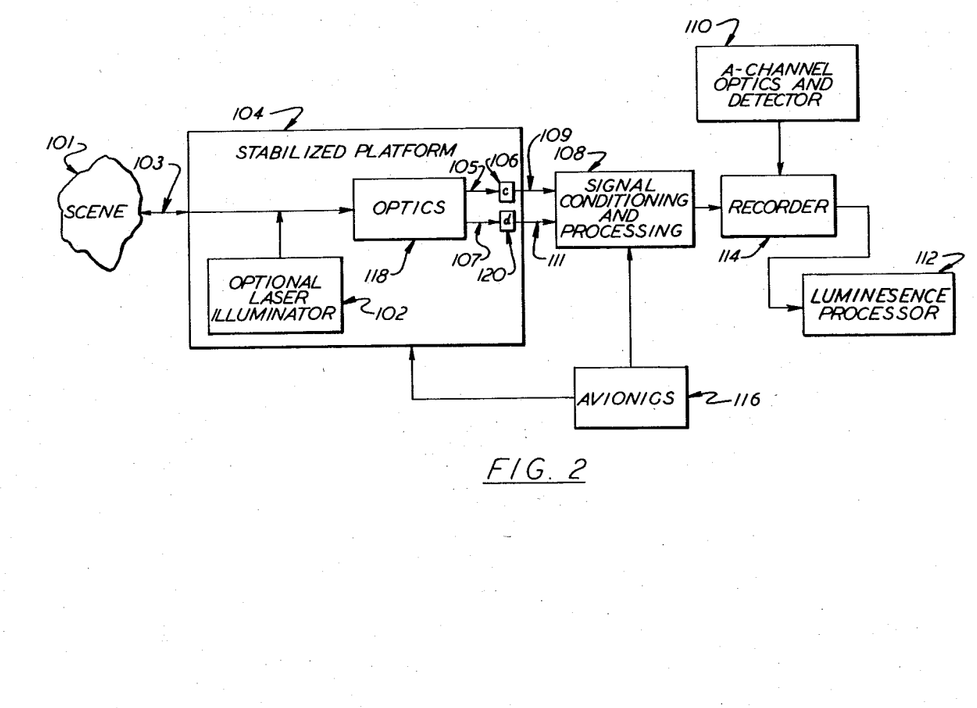
FIG. 2 is a block diagram of a Fraunhofer line discriminator according to the present invention.

Referring now to FIG. 2, it can be seen that radiation 103 (composed of reflected and luminescent components) enters the optics 118. The optics 118 are for determining luminescence at a single Fraunhofer line frequency, e.g., 5890 angstroms, and contain a c-channel and a d-channel. The terms c-channel and d-channel refer to the optics and detectors used to select and detect the c and d light intensity, respectively, described in reference to FIG. 1B. Practice has shown that the ratio of b/a can be fixed during much of the day. Following the optics 118 are two beam paths 105 and 107. Beam path 105 falls incident on c-channel detector array 106 and beam path 107 falls incident on the d-channel detector array 120. Each of the detectors 106 and 120 is an array of mxn detector elements with an image of the scene 101 projected on it. Thus each point in the scene is sampled for c and d light intensity value a predetermined number of times. The optics 118, beam paths 105 and 107 and detector arrays 106 and 120 are more fully described in reference to FIGS. 3, 4A and 4B hereinbelow.

FIG. 2 also shows that an optional laser illuminator 102 can be provided to illuminate the scene 101. The laser illuminator 102 extends the use of the present invention to night-time operations. In addition, since materials are excited and fluoresce at specific unique frequencies the proper selection of a excitation laser frequency and detection for fluorescence at a specific frequency allows one to identify precisely a given material. In the form of the present invention that includes an optional laser illuminator 102, the c-channel optics are used to detect laser light reflected from the ground while the d-channel optics detect luminescence induced by the laser light. As explained more fully hereinbelow, in reference to FIGS. 3, 4A and 4B the c-channel and d-channel optics are modified when a laser illuminator is employed to accomplish the foregoing. As is known in the art of fluorescence spectroscopy, a material emits a characteristic emission spectrum in response to exciting radiation, such as the laser here employed. Accordingly, the c-channel optics look at the emission spectrum while the d-channel optics sense the exciting radiation. The radiation detection and processing are equivalent to that described hereinbelow in reference to Fraunhofer line detection.

The optics 118, detector arrays 106 and 120 and the optional laser illuminator 102 are all mounted on a stabilized platform 104. The stabilized platform maintains the line of sight of the optics 118 to the scene 101, in response to signals from the aircraft's avionics 116, in a manner explained in reference to FIG. 5.

The analog outputs 109 and 111 from the detector arrays 106 and 120, respectively, and signals from the aircraft's avionics 116 are fed to the signal conditioning and processing unit 108. The signal conditioning and processing unit 108 performs amplification, digitizing, co-adding and logic tasks in a manner explained in reference to FIG. 7.

The conditioned and processed signals, along with the a-channel intensity levels from the a-channel optics and detector 110, are recorded by recorder 114. A-channel optics, of course, selects and detects the "a" value of light intensity as described in reference to FIG. 1A.

The data recorded by recorder 114 can then be accessed by luminescence processor 112 which then solves equation 1 for luminescence at each point in the scene.

Figure 3:
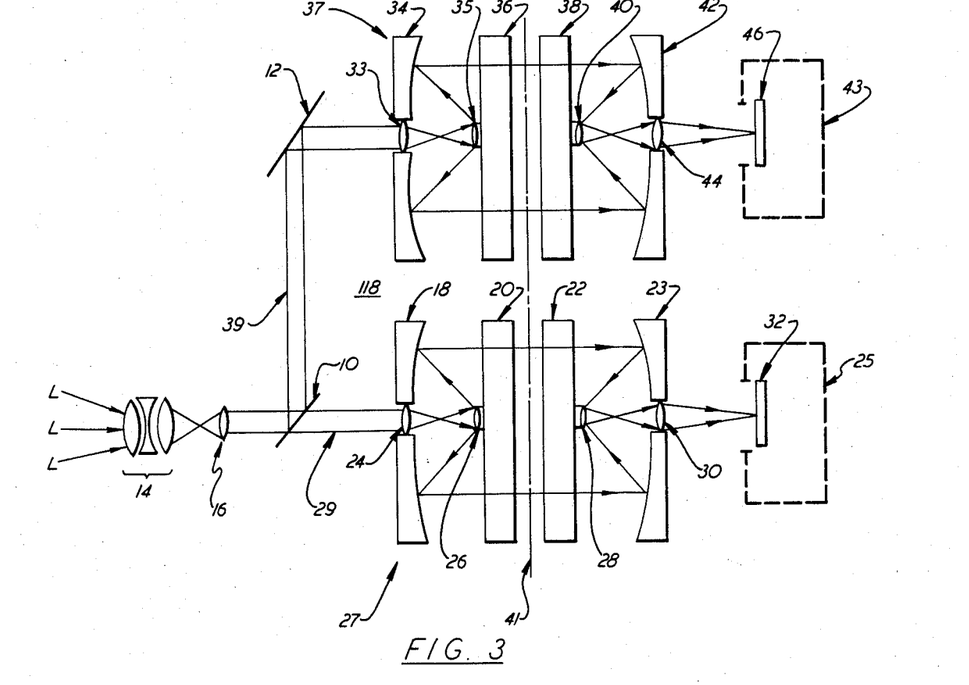
FIG. 3 shows, in schematic form, an optical assembly for a Fraunhofer line discriminator according to the present invention.

FIG. 3 is a schematic drawing of one form of the optics 118 of FIG. 2.

Light from the scene being viewed, designated 'L', enters collecting optics 14. Collecting optics 14 is a wide angle lens assembly which determines the field of view. It is selected based on the area and resolving power of the narrow-band etalon described hereinbelow.

Following the collecting optics 14 is a collimating lens 16 which collimates the beam of light coming from the collecting optics.

The collimated beam then falls incident on a beam-splitter 10. The beam-splitter 10 divides the collimated beam into two components 29 and 39, each of which is at a different amplitude, which amplitude is determined in a manner described hereinbelow.

Beam component 29, after passing through the beam-splitter 10, enters the c-channel optics 27. Beam component 39, after after being reflected by the beam-splitter 10, is reflected by folding mirror 12 into the d-channel optics 37.

Turning now to the c-channel optics 27 it can be seen that beam component 29 falls incident on the field stop/lens 24 which directs the light incident thereon to the secondary mirror 26. The secondary mirror 26 then directs the light to the primary mirror 18 which collimates the beam for passage through the blocking filter 20 and Fabry-Perot etalon 22.

Both blocking filter 20 and Fabry-Perot etalon 22 have a passband centered on the Fraunhofer line being detected. The blocking filter 20 is preferably placed between the collecting optics 14 and the Fabry-Perot etalon 22 so as to restrict the amount of excess sunlight reflecting between the etalon 22 and the filter 20. The blocking filter 20 is a narrow passband filter of, e.g., 10 angstroms centered on the desired Fraunhofer line. The blocking filter 20 functions to prevent spectral aliasing and blocks the multiple pass bands of the Fabry-Perot etalon 22. As is known in the art, the width of the blocking filter 20 is determined by the foregoing blocking filter requirements which are, in turn, determined by the Fabry-Perot etalon design. The Fabry-Perot etalon 22 is constructed of a solid glass spacer with partially reflecting surfaces on either side. As is known in the art, evidenced by U.S. Pat. No. 3,578,848, the bandpass of the Fabry-Perot etalon 22 is determined principally by the thickness of its glass spacer. Passbands of 1 angstrom or less, centered on the desired Fraunhofer line, are attainable.

In order to maintain the center wavelength associated with each etalon in the region of a Fraunhofer line, it is necessary to tightly control the temperature of the Fabry-Perot etalon 22. Therefore, a heater, not shown, is provided to maintain the Fabry-Perot etalon 22 at a constant temperature.

The light of narrow passband centered on the desired Fraunhofer line, then passes out of the Fabry-Perot etalon 22 and falls incident on primary mirror 23. The light is reflected by primary mirror 23 onto secondary mirror 28 which reflects the light onto re-imaging lens 30 which, in the form shown, is constrained within the substrate of the primary mirror 23.

Re-imaging lens 30 passes the light and forms an image of the scene 101 being viewed onto c-channel detector array 32.

The components in the c-channel optics 27 are symmetrically located about centerline 41. Centerline 41 is parallel to and equidistant from both blocking filter 20 and Fabry-Perot etalon 22. Consequently, the image of the scene 101 being viewed formed by lens 24 is the same as the image formed by re-imaging lens 30 onto the detector array 32 with the exception that only a narrow band of energy, centered around the desired Fraunhofer line, will be imaged by reimaging lens 30 onto the detector array 32.

The detector array 32 is best composed of, for example, silicon sensors for detection of wavelengths below 1 $\mu$m. The dark current of silicon sensors is strongly temperature dependent, accordingly a refrigerator 25 is provided to hold the dark current to a constant during all operating conditions.

The geometry of the d-channel optics 37 is similar to that of the c-channel optics and is also symmetric about centerline 41. Beam 39 is directed by folding mirror 12 onto lens 33 where an image of the scene being viewed is formed.

The light then is imaged onto secondary mirror 35 whereupon it is reflected to the primary mirror 34 which collimates the light for passage through the blocking filter 36 and blank 38.

The blocking filter 36 is equivalent to the blocking filter 20, that is, a narrow passband filter of, e.g., 10 angstroms centered on the desired Fraunhofer line. Since the widths of Fraunhofer lines are significantly less than 10 angstroms, radiation in the continuum outside the Fraunhofer line is predominantly passed through the blocking filter 36 in addition to any radiation inside the Fraunhofer line.

The light then passes through the blank 38 which transmits all the radiation from the blocking filter 36. The light emanating from the blank 38 falls incident on the primary mirror 42, whereupon it is reflected to the secondary mirror 40 which, in turn, forms an image before the reimaging lens 44 equivalent to that formed by lens 33. Reimaging lens 44 is, in the form shown, constrained within primary mirror 42.

Re-imaging lens 44 then forms an image of the scene being viewed on the d-channel detector array 46. As in the case of the c-channel detector array 32, and for the same reason, the d-channel detector array is housed in a refrigerated compartment 43.

The c-channel optics 27 and d-channel optics 37 are geometrically identical so that there are no distortion or magnification differences between them. In addition, the radiation through-put is equalized by selecting an appropriate beam-splitter 10.

Since the c-channel optics 27 have a narrow passband Fabry-Perot etalon 22 in place of the blank 38 of the d-channel optics 37 the transmission of the c-channel optics 27 is proportionately reduced. The beam splitter 10 thus passes more radiation along beam path 29 than along beam path 39 to provide for equal radiation transmission through the c-channel optics 27 and d-channel optics 37.

To further control any errors that could occur between the c-channel array 32 and d-channel array 46 the two refrigerated compartments 25 and 43, respectively, are controlled to substantially the same temperature.

In addition, the c-channel and d-channel detector arrays, 32 and 46, are held to close mechanical tolerances to ensure that they are registered to one another, that is, to ensure that the scene being viewed is viewed, spatially, in the same way on each detector array.

As discussed hereinabove in reference to FIG. 2, the passband of the c-channel optics is modified when an optical laser illuminator is employed. In this case, the c-channel optics would have a passband on the order of 100-1000 A, centered on the emission spectrum of the material as excited by the laser radiation. The d-channel optics have a passband which allows the exciting laser radiation to pass therethrough.

Figure 4A:
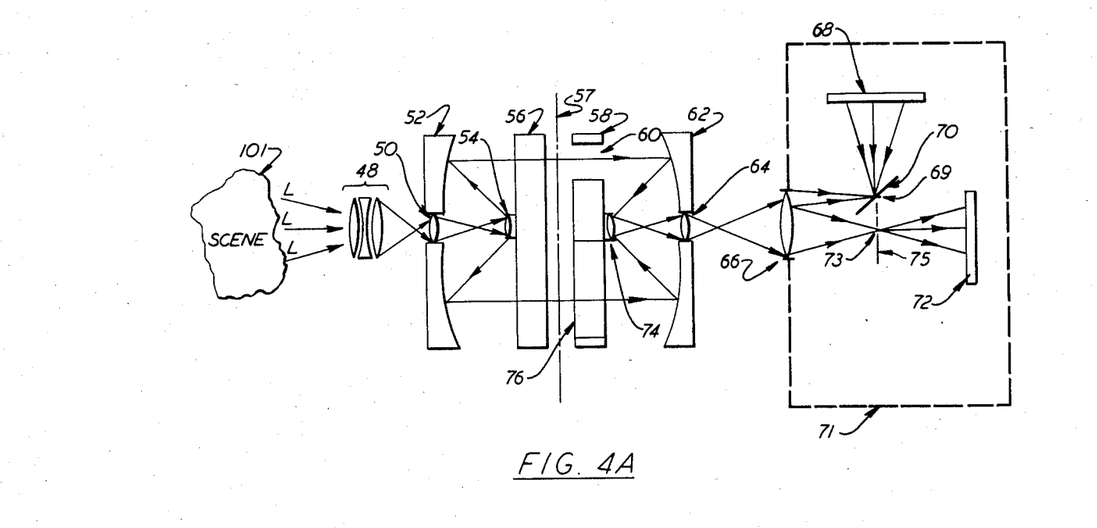
FIG. 4A shows, in schematic form, an optical assembly for a Fraunhofer line discriminator according to the present invention.

FIG. 4A show schematically another form of the optics suitable for use in the present invention.

As in the optical configuration of FIG. 3 the optical components of FIG. 4A are symmetrically located about a centerline 57.

The collecting optics 48 collect incoming light, designated 'L' from a scene 101 being viewed. The scene 101 is imaged by collecting optics 48 on field lens 50 which controls the pupil of the system. The primary mirror 52 and secondary mirror 54 are, for example, in a Cassegrain configuration with the secondary mirror 54 being a hyperboloidal mirror reflecting the image from field lens 50 onto the paraboloidal primary mirror 52 which substantially collimates the beam of light.

The collimated beam then passes through blocking filter 56 and c, d-channel multiplexer 58, the operation of which is explained below in reference to FIG. 4B.

After passing through the c, d-channel multiplexer 58 the collimated beam is reflected by primary mirror 62 to secondary mirror 74 which then focuses the beam on field lens 64. Primary mirror 62, secondary mirror 74 and field lens 64 are similar to primary mirror 52, secondary mirror 54 and field lens 50, respectively in terms of geometry and function.

The field lens 64 serves to reimage the system pupil onto the c, d demultiplexer mirror 70 in conjunction with the single refractive imager 66 which both matches the focal length of the system to detector array size and serves as a window to the refrigerated enclosure 71.

The refractive imager 66 forms an image of the light emerging from the c, d multiplexer 58 in the form of two spots 69 and 73 of light at plane 75. Spot 69 is the focused beam of light passing through opening 60 and spot 73 is the focused beam of light emerging from Fabry-Perot etalon 76. Spot 73 expands forming an image of the scene 101 being viewed at c-detector array 72. Spot 69 is directed by c, d demultiplexer mirror 70 to d-detector array 68. Refrigerated enclosure 71 is equivalent in function and structure to refrigerated enclosures 25 and 43 previously described in reference to FIG. 3.

Figure 4B:
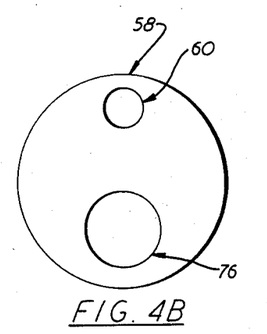
FIG. 4B is a plan view of an optical multiplexer useful in the optical assembly of FIG. 4A.

FIG. 4B shows a plan view of channel multiplexer 58 of FIG. 4A. The surface of the c, d-channel multiplexer 58 nearest the blocking filter 56 is made opaque except for opening 60 and Fabry-Perot etalon 76. In this way light emanating from blocking filter 56 passes through only opening 60 and Fabry-Perot etalon 76.

The Fabry-Perot etalon 76 and opening 60 are sized with respect to each other to equalize the through-put of radiation through each in the same manner as described in reference to the c-channel optics 27, d-channel optics 37 and beamsplitter 10 of FIG. 3.

In this manner the images formed at d-detector array 68 and c-detector array 72 of FIG. 4A are equivalent to the images formed at c-detector array 32 and d-detector array 46 described in reference to FIG. 3.

The c-channel and d-channel optics of FIGS. 4A and 4B can be modified in the same manner as the c-channel and d-channel optics of FIG. 3 when an optional laser illuminator is employed.

Figure 5:
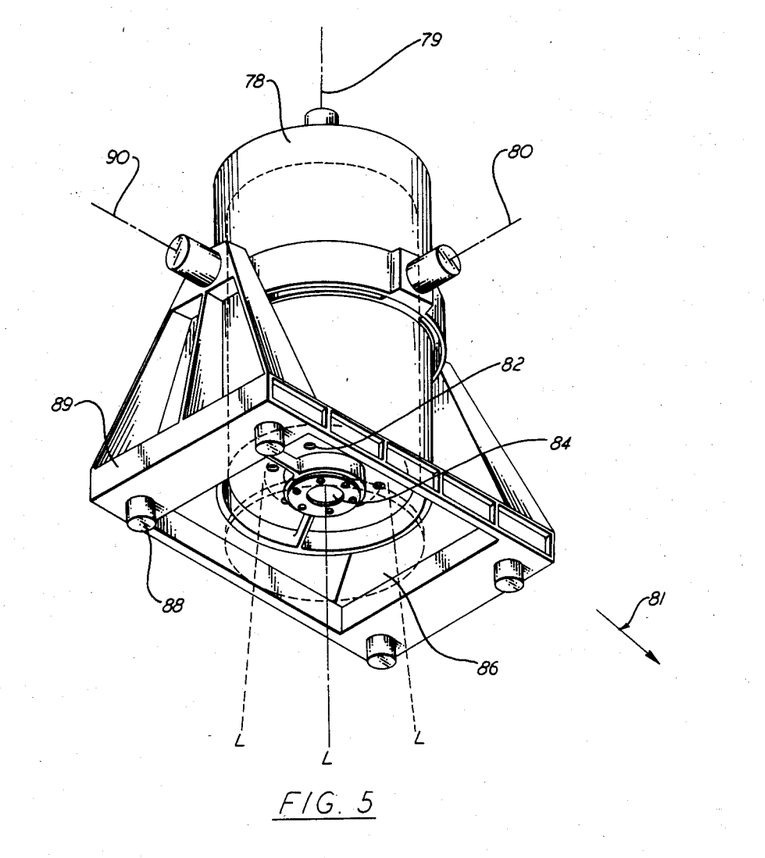
FIG. 5 is an isometric drawing of Fraunhofer line detector subsystem shown mounted on a stable platform.

FIG. 5 shows one possible housing 79 and stabilizing platform 89 for the optics and detectors of FIG. 3 or FIG. 4A.

The stabilized platform is isolated from shocks by shock absorbers 88 and stabilizes the housing 78 about three axes: roll 90, pitch 80 and yaw 79. The direction of movement of the aircraft is as shown by arrow 81.

The aircraft has a window 86 through the fuselage thereof to permit light, designated 'L', from the scene being viewed to pass through the stabilized platform 89 to the Fraunhofer line wavelength channels 82 and window 84.

In the form shown the housing contains, for example, six Fraunhofer line wavelength channels 82. Each of these Fraunhofer line wavelength channels 82 contain one c-channel and one d-channel. In addition, the housing 78 contains, for example, a window 84 for a television camera.

Avionics 116, as shown in FIG. 2, provide the input to means, not shown, which cause the housing 78 to rotate about the roll 90, pitch 80 and yaw axes 79 in equal and opposite reaction the aircraft movements. In this manner the lines of sight of the Fraunhofer line wavelength channels 82 remain substantially parallel to themselves no matter what orientation the aircraft takes as it progresses. This stabilization allows the co-adding of elements in the manner described hereinbelow. The avionics 116 may be common to the aircraft's control system or can be discrete pitch, roll and yaw sensors located near or on the stabilized platform 89.

Figure 6A:
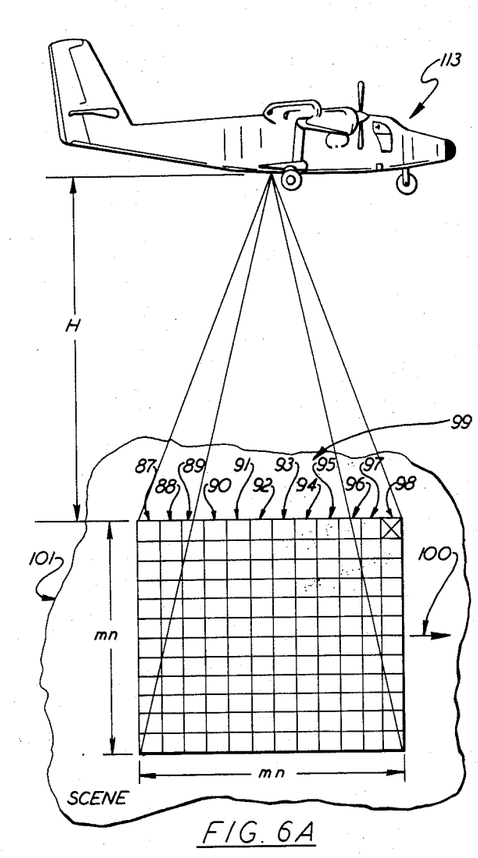
FIGS. 6A and 6B are schematic representations of the time delayed integration, off-chip co-add concept according to the present invention.
Figure 6B:
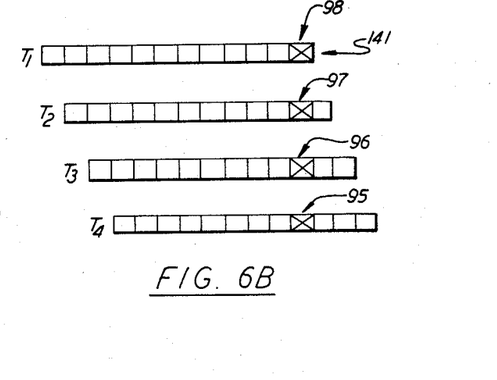
Figure 7:
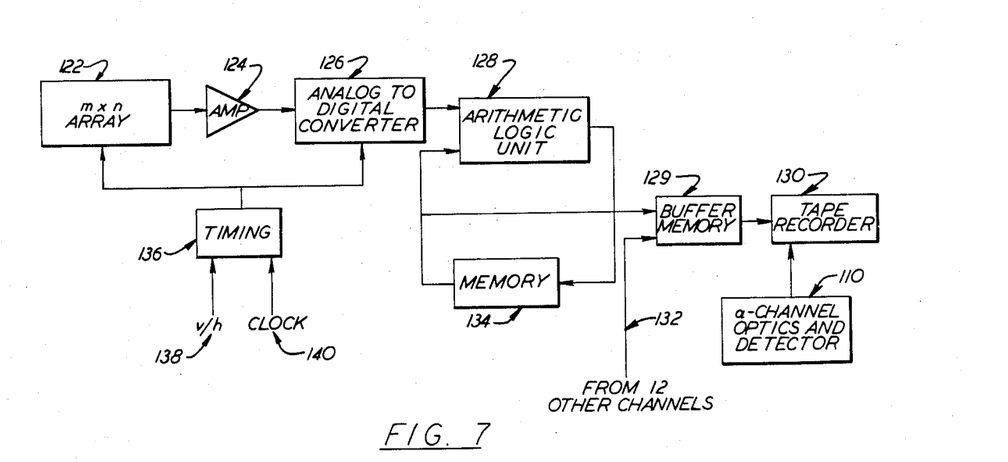
FIG. 7 is a block diagram of the optical, sensing, data acquisition and processing steps according to the present invention.

The concept of co-adding or off-chip time delayed integration can now be explained in reference to FIGS. 6A, 6B and 7.

FIG. 6A shows an aircraft 113 flying over a scene 101 at an altitude designated 'H'. A Fraunhofer line detector of the type shown in FIG. 5, is carried by the aircraft 113 and views that portion of the scene 101 demarcated by the grid 99.

The grid 99 is divided into mxn elements. In the example shown in FIG. 6A there are $12 \times 12$ or 144 elements in the grid 99. All of the n-columns of elements are termed a cross-track swath since they cross, at a right angle, the track or direction 100 taken by the aircraft 113. Similarly, the m-rows comprise along-track swathes since they parallel the track or direction 100 of the aircraft 113. Accordingly, elements 87-98 comprise one row in the along-track swath.

Each of the mxn grid elements defines a unique point on the ground at each time interval. For instance, at time $T_1$, grid element 98 defines the ground point designated 'X'. At successive time intervals $T_2$, $T_3$, $T_4$... the ground point 'X' underlays adjacent elements 97, 96, 95 ... in the along-track swath.

The movement of the grid 99 over the scene 101 being viewed is shown conceptually in FIG. 6B. At time $T_1$ the first along-swath row 141, which comprises elements 87-98, has ground point 'X' underlaying element 98. At time $T_2$ the along-swath row 141 has moved one element and ground-point 'X' underlays element 97. In succession then at time $T_3$ the ground point 'X' is at element 96 and at $T_4$ it is at element 95. This continues until time $T_{12}$ at which point the ground point 'X' underlays element 87. At time $T_{13}$ no grid element overlays ground point 'X'. Hence, the Fraunhofer line detector is no longer viewing ground point 'X' in the scene. The determination of the time interval between $T_1$, $T_2$, $T_3$, $T_4$... $T_{12}$ is a function of the velocity, V, and altitude, H, of the aircraft 113 flying over the scene in the direction 100 and is discussed in reference to FIG. 7.

The grid 98 is imaged onto the detectors 68 and 72 of FIG. 4A or the detectors 32 and 46 of FIG. 3 as described in reference to FIGS. 4A and 3, respectively. Accordingly, each element of the grid 99 of FIG. 6A corresponds to a unique location on the detector arrays 68 and 72 or 32 and 46. The signals from these unique array locations are then co-added and processed, in a manner hereinbelow described in reference to FIG. 7, for the fluorescence at each groundspot, such as 'X' of FIG. 6A, in the along-track swath.

It can be appreciated by those skilled in the art that the registration of the c-channel detector array to the d-channel detector array is achieved through the proper alignment of the optical assemblies of FIGS. 3 or 4A. In this way, for each time interval, elements in the c-channel detector array are registered to corresponding elements in the d-channel detector array. In this context registration means that corresponding d-channel and c-channel detector elements are viewing the same ground point, 'X'.

FIG. 7 is a flow-chart which illustrates the manner in which the signals from the detector arrays are conditioned and processed. The mxn array 122 is representative of any one of the detector arrays 68 or 72 of FIG. 4A or 32 or 46 of FIG. 3.

The video amplifier 124 buffers the analog signals generated by the mxn detector array 122 and raises these signals to a suitable transmission level to the analog to digital converter 126. The analog to digital converter 126 converts all analog inputs into digital values for subsequent processing in the arithmetic logic unit 128.

The timing for sampling the mxn array 122 and converting the sampled analog signals to digital values is controlled by timing device 136. A constant clock rate from clock 140 would cause cumulative spatial errors or element overlap and therefore reduce the efficiency of co-adding since the velocity, 'V', and height, 'H', of the platform vary. Consequently the timing rate from the timing device 136 is altered in response to a V/H signal 138 from the aircraft's avionics 116 of FIG. 2. This control is achieved straightforwardly by phase locking the timing signal from the timing device 136 to the derived V/H rate.

V/H can be determined by using aircraft avionics 116 to measure velocity and height separately or by using the signal from a V/H meter of the type known in the arts of aerial reconnaissance and surveying.

The arithmetic logic unit 128 performs the co-adding function. As explained in reference to FIGS. 6A and 6B each pixel on the grid 98 of the scene being viewed is imaged at a unique location or pixel on the detector array 122. The radiation intensity at a unique point on the ground, such as 'X' of FIG. 6A, can then be sampled a plurality of times equal to the number of elements in the grid 99 of FIG. 6A in an along track swath. At each sampling interval $T_1$, $T_2$, $T_3$... the intensity of value from the ground point is stored in memory 134. The intensity at the same point on the ground is sampled a plurality of times, added then averaged in the arithmetic logic unit 128.

This averaged intensity value for a unique ground location is stored in buffer memory 129 along with the values from the 11 other channels 132. These 12 values, along with the value from the a-channel optics and detector 110 are then stored on, for example, a tape recorder 130.

These values can then be used, in any convenient manner, by the luminescence processor 112 to calculate the luminescence value using equation 1.

Other modifications of the present invention are possible in light of the above description which should not be construed as placing limitations on the invention other than those specifically set forth in the claims which follow.

What is claimed is:

1. An apparatus for determining fluorescence of materials in a scene being viewed comprising:
   means forming a first beam path and a second beam path, each passing radiation from said scene being viewed;
   a first broad filter centered on said Fraunhofer line with a passband extending into the solar continum on either side of said Fraunhofer line and a narrow filter centered on said Fraunhofer line having a narrow passband, on the order of half the width of said Fraunhofer line at half depth of said Fraunhofer line;
   a multiplexer;
   said narrow filter being constrained within said multiplexer, said multiplexer having an aperature therethrough which passes radiation in said second beam path;
   said first beam path passing through said first broad filter and said narrow filter;
   imaging means forming an image of the radiation traversing said first and second beam paths onto first and second detector arrays, respectively the image on the first detector array being in registration with the image on the second detector array;
   a single detector to detect the intensity of direct solar radiation outside the Fraunhofer line; and
   processing means connected to said first and second detector arrays and said detector to determine the level of fluorescence in the scene being viewed.

2. An apparatus according to claim 1 wherein said processing means comprises:
   an analog-to-digital converter to convert the analog signal from said first detector array, said second detector array and said single detector to digital values;
   timing means to control the sampling interval of the first and second detector arrays;

co-adding means to add the intensity value at one pixel on each of the first and second detector array corresponding to a point in said scene to the value detected at adjaent pixels on each of the first and second detector arrays corresponding to the same point in said scene after subsequent time intervals.

3. An apparatus as claimed in claim 2 which further includes:

means for compute the average intensity value corresponding to a point in said scene for all of said pixels co-added.

4. An apparatus as claimed in claim 1 wherein said narrow filter comprises:

a Fabry-Perot etalon.

5. An apparatus according to claim 1 wherein said imaging means comprises:

imaging means to form an image of said multiplexer at the focal plane of said imaging means;

demultiplexer mirror to direct the radiation from said second beampath to said second detector array;

the radiation from said first beam path expanding from said focal plane to said first detector array.

6. An apparatus according to claim 1 wherein said means to form said first beam path and said second beam path is a beam splitter.

7. An apparatus as claimed in claim 1 wherein said first and second detector arrays are silicon.

8. An apparatus as claimed in claim 7 wherein the temperature of said first and second detector arrays is absolutely and relatively controlled.

9. An apparatus as claimed in claim 1 wherein said single detector is silicon.

10. An apparatus as claimed in claim 9 wherein the temperature of said single detector is absolutely controlled.

11. An apparatus as claimed in claim 1 wherein said processing means computes the intensity of solar stimulated fluorescence at each point in the scene being viewed in accordance with the formula:

$$L = \frac{1}{a} \frac{(c - nd)}{(1 - n)}$$

where:
L = Fluorescence
a = intensity of direct solar radiation
c = average intensity detected by said first detector array
d = average intensity detected by said second detector array
n = a constant representative of the depth of the Fraunhofer line.

12. An apparatus for determining fluorescence of materials in a scene being viewed illuminated by laser radiation comprising:

means forming a first beam path and a second beam path, each passing radiation from said scene being viewed;

a first broad filter center on the emission spectrum of said material with a passband extending into the electromagnetic spectrum on either side of said emission spectrum and a narrow filter centered on said emission spectrum of said material having a narrow passband within the emission spectrum of said material;

a multiplexer;

said narrow filter being constrained within said multiplexer, said multiplexer having an aperature therethrough which passes radiation in said second beam path;

said first beam path passing through said first broad filter and said narrow filter;

imaging means forming an image of the radiation traversing said first and second beam paths onto first and second detector arrays, respectively, the image on the first detector array being in registration with the image on the second detector array;

a single detector to detect the intensity of direct solar radiation outside the Fraunhofer line; and processing means connected to said first and second detector arrays and said detector to determine the level of fluorescence in the scene being viewed.

13. An apparatus according to claim 12 wherein said processing means comprises:

an analog-to-digital converter to convert the analog signal from said first detector array and said second detector array to digital values;

timing means to control the sampling interval of the first and second detector arrays;

co-adding means to add the intensity value at one pixel on each of said first and second detector arrays corresponding to a point in said scene to the value detected at adjacent pixels on each of said first and second detector arrays corresponding to the same point in said scene after subsequent time intervals.

14. An apparatus as claimed in claim 13 which further includes:

means to compute the average intensity value of a point in said scene for all of said pixels co-added.

15. An apparatus according to claim 12 wherein said imaging means comprises:

imaging means to form an image of said multiplexer at the focal plane of said image means;

a demultiplexer mirror to direct the radiation from said second beampath to said second detector array;

the radiation from said first beam path expanding from said focal plane to said first detector array.

16. An apparatus according to claim 12 wherein said means to form said first beam path and said second beam path is a beam splitter.

17. An apparatus as claimed in claim 12 wherein first and second detector arrays are silicon.

18. An apparatus as claimed in claim 17 wherein the temperature of said first and second detector arrays is absolutely and relatively controlled.

* * * * *